United States Patent
Fan et al.

(10) Patent No.: US 9,103,727 B2
(45) Date of Patent: Aug. 11, 2015

(54) COMPOSITE FABRY-PÉROT SENSOR

(71) Applicant: The Regents of the University of Michigan, Ann Arbor, MI (US)

(72) Inventors: Xudong Fan, Saline, MI (US); Karthik Reddy, Ann Arbor, MI (US); Yunbo Guo, Austin, TX (US)

(73) Assignee: The Regents of The University of Michigan, Ann Arbor, MI (US)

( * ) Notice: Subject to any disclaimer, the term of this patent is extended or adjusted under 35 U.S.C. 154(b) by 146 days.

(21) Appl. No.: 13/729,983

(22) Filed: Dec. 28, 2012

(65) Prior Publication Data

US 2013/0169970 A1 Jul. 4, 2013

Related U.S. Application Data

(60) Provisional application No. 61/582,620, filed on Jan. 3, 2012.

(51) Int. Cl.
| | | |
|---|---|---|
| *G01B 9/02* | (2006.01) | |
| *G01J 3/45* | (2006.01) | |
| *G01N 21/27* | (2006.01) | |
| *G01N 21/39* | (2006.01) | |
| *G01N 30/74* | (2006.01) | |

(52) U.S. Cl.
CPC ............. *G01J 3/45* (2013.01); *G01N 21/274* (2013.01); *G01N 21/39* (2013.01); *G01N 30/74* (2013.01)

(58) Field of Classification Search
USPC ............ 356/454, 506, 519, 114; 385/12–14
See application file for complete search history.

(56) References Cited

U.S. PATENT DOCUMENTS

| | | | |
|---|---|---|---|
| 5,381,231 A | * | 1/1995 | Tu ................................. 356/480 |
| 7,623,234 B2 | | 11/2009 | Puzey |

(Continued)

FOREIGN PATENT DOCUMENTS

| | | |
|---|---|---|
| WO | 2012/096955 A1 | 7/2012 |
| WO | 2013/070954 A1 | 5/2013 |

OTHER PUBLICATIONS

Agah, Masoud, et al., "High-Performance Temperature-Programmed Microfabricated Gas Chromatography Columns," Journal of Microelectromechanical Systems, vol. 14, No. 5, pp. 1039-1050 (Oct. 2005).

(Continued)

*Primary Examiner* — Tri T Ton
(74) *Attorney, Agent, or Firm* — Harness, Dickey & Pierce, P.L.C.

(57) ABSTRACT

A self-referencing composite Fabry-Pérot cavity sensor, including methods of use and manufacture. The cavity sensor comprises a substrate defining a first cavity portion juxtaposed to a second cavity portion. The first and second cavity portions are provided having a predetermined depth offset. A polymer or other dielectric material is disposed within the first and second cavity portions. An interference spectrum resulting from a light source of a known wavelength is reflected through the sensor and produces a first refractive index from the first cavity portion offset by a second refractive index from the second cavity portion. The difference in refractive indices can be used to determine various physical parameters. An optical sensor according to the present technology may be used with vapor sensing, pressure sensing, protein detection, photo-acoustic imaging, and the like.

14 Claims, 7 Drawing Sheets

(56) References Cited

U.S. PATENT DOCUMENTS

| | | | |
|---|---|---|---|
| 7,894,057 | B2 | 2/2011 | Puzey |
| 8,178,355 | B2 | 5/2012 | Acharya et al. |
| 2006/0073483 | A1 | 4/2006 | White et al. |
| 2007/0227907 | A1 | 10/2007 | Shah et al. |
| 2014/0017700 | A1 | 1/2014 | Fan et al. |
| 2014/0298990 | A1 | 10/2014 | Fan et al. |

OTHER PUBLICATIONS

Beard, P.C., "Interrogation of free-space Fabry-Perot sensing interferometers by angle tuning," Measurement Science and Technology, vol. 14, No. 11, pp. 1998-2005 (Sep. 19, 2003) (downloaded on Dec. 22, 2011).

Gauglitz, G., et al., Chemical and biochemical sensors based on interferometry at thin (multi-)layers, Sensors and Actuators B, vol. 11, pp. 21-27 (1993).

Hou, Yang, et al., "Thin polymer etalon arrays for high-resolution photoacoustic imaging," Journal of Biomedical Optics, vol. 13, No. 6, pp. 064033-1-064033-8 (Nov./Dec. 2008) (published online Dec. 23, 2008).

Lambertus, Gordon R., et al., "Silicon Microfabricated Column with Microfabricated Differential Mobility Spectrometer for GC Analysis of Volatile Organic Compounds," Analytical Chemistry, vol. 77, No. 23, pp. 7563-7571 (Dec. 1, 2005) (published online Oct. 25, 2005).

Liu, Jing, et al., "Fabry-Pérot Cavity Sensors for Multipoint On-Column Micro Gas Chromatography Detection," Analytical Chemistry, vol. 82, No. 11, pp. 4370-4375 (Jun. 1, 2010) (published online May 4, 2010).

Liu, Jing, et al., "Highly versatile fiber-based optical Fabry-Pérot gas sensor," Optics Express, vol. 17, No. 4, pp. 2731-2738 (Feb. 16, 2009) (published online Feb. 10, 2009).

Martínez-Hipatl, Carlos, et al., "Detection of volatile organic compounds by an interferometric sensor," Sensors and Actuators B: Chemical, vol. 147, pp. 37-42 (2010) (published online Mar. 17, 2010).

Noh, Hong-seok, et al., "Parylene Gas Chromatographic Column for Rapid Thermal Cycling," Journal of Microelectromechanical Systems, vol. 11, No. 6, pp. 718-725 (Dec. 2002).

Özkumur, Emre, et al., "Label-free and dynamic detection of biomolecular interactions for high-throughput microarray applications," Proceedings of the National Academy of Sciences of the United States of America, vol. 105, No. 23, pp. 7988-7992 (Jun. 10, 2008).

Reddy, Karthik, et al., "On-chip Fabry-Pérot interferometric sensors for micro-gas chromatography detection," Sensors and Actuators B: Chemical, vol. 159, pp. 60-65 (2011) (published online Jun. 15, 2011).

Reddy, Karthik, et al., "Rapid, sensitive, and multiplexed on-chip optical sensors for micro-gas chromatography," Lab on a Chip, vol. 12, No. 5, pp. 901-905 (Mar. 7, 2012) (published online Jan. 16, 2012) (downloaded on Jan. 3, 2013).

Reddy, Karthik, et al., "Self-referenced composite Fabry-Pérot cavity vapor sensors," Optics Express, vol. 20, No. 2, pp. 966-971 (Jan. 16, 2012) (published online Jan. 4, 2012).

Reichl, D., et al., "Sensing of Volatile Organic Compounds Using a Simplified Reflectometric Interference Spectroscopy Setup," Applied Spectroscopy, vol. 54, No. 4, pp. 583-586 (2000).

Reidy, Shaelah, et al., "Temperature-Programmed GC Using Silicon Microfabricated Columns with Integrated Heaters and Temperature Sensors," Analytical Chemistry, vol. 79, No. 7, pp. 2911-2917 (Apr. 1, 2007) (published online Feb. 21, 2007).

Terry, Stephen C., et al., "A Gas Chromatographic Air Analyzer Fabricated on a Silicon Wafer," Institute of Electrical and Electronics Engineers Transactions on Electron Devices, vol. ED-26, No. 12, pp. 1880-1886 (Dec. 1979).

Zellers, Edward T., et al., "Optimal Coating Selection for the Analysis of Organic Vapor Mixtures with Polymer-Coated, Surface Acoustic Wave Sensor Arrays," Analytical Chemistry, vol. 67, No. 6, pp. 1092-1106 (Mar. 15, 1995) (Abstract published in Advance ACS Abstracts, Feb. 1, 1995).

\* cited by examiner

Figures 1(A) and (B)

Figures 3(A)-(D)

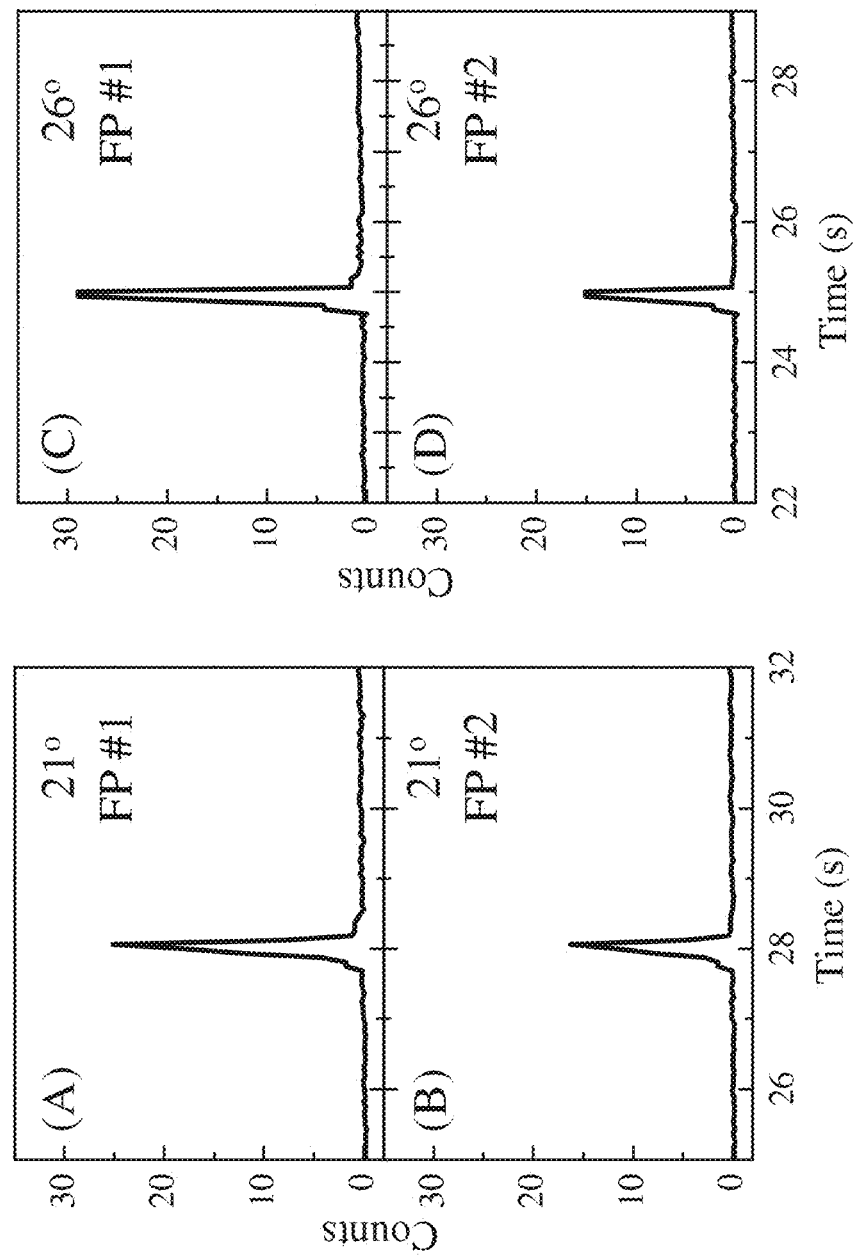
Figures 6(A)-(D)

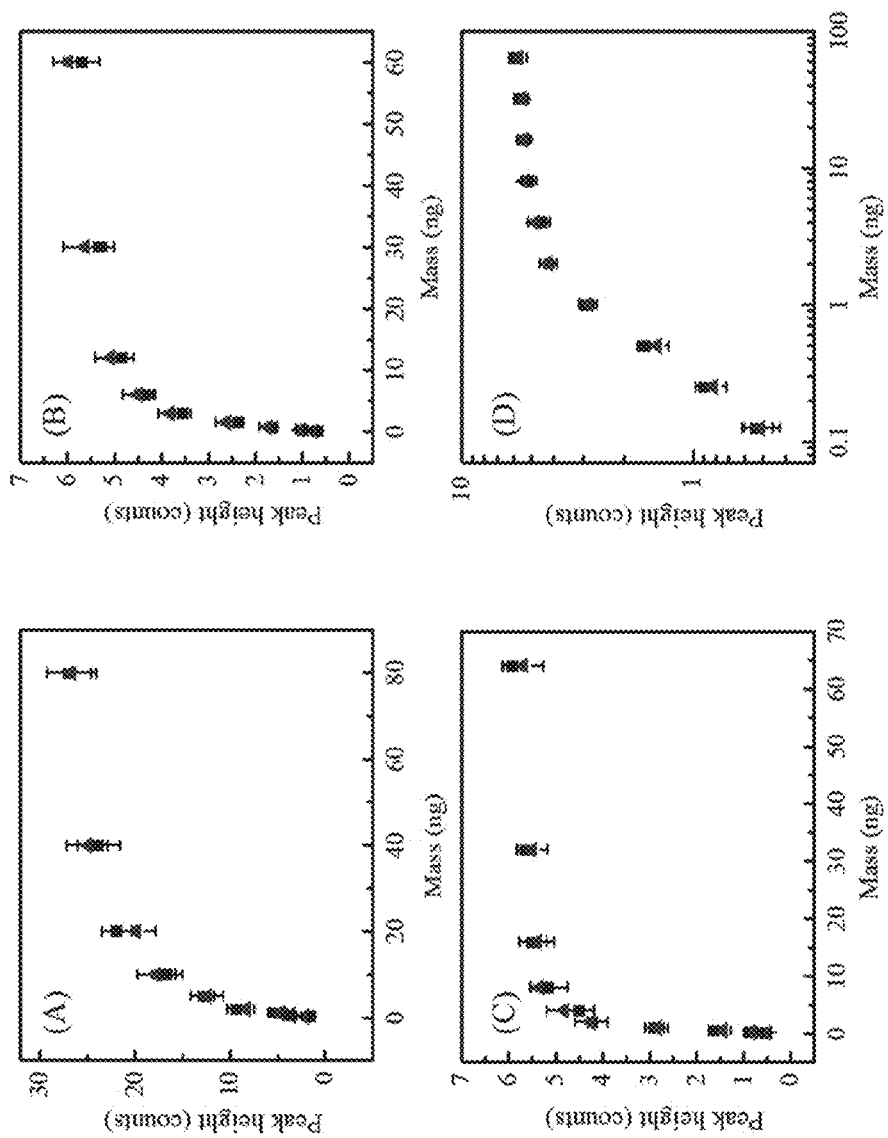
Figure 7(A)-(D)

COMPOSITE FABRY-PÉROT SENSOR

CROSS-REFERENCE TO RELATED APPLICATIONS

This application claims the benefit of U.S. Provisional Application No. 61/582,620, filed on Jan. 3, 2012. The entire disclosure of the above application is incorporated herein by reference.

GOVERNMENT RIGHTS

This invention was made with government support under IOS0946735 awarded by the National Science Foundation. The government has certain rights in the invention.

FIELD

The present disclosure relates to optofluidic based sensors, and more specifically to Fabry-Pérot based structures, including applications and fabrications of the same.

BACKGROUND AND SUMMARY

Fabry-Pérot based structures can be used to detect a variety of optics and measurements, as well as for determining strain, temperature, acoustic waves, and various other properties and physical parameters. The present technology provides a self-referencing composite Fabry-Pérot cavity sensor. According to various aspects of the present technology, the composite Fabry-Pérot cavity sensor is able to detect a change in thickness and refractive index of a dielectric material upon exposure to a sample, allowing for accurate measurement detections regardless of the dielectric material thickness, refractive index, light incident angle, and wavelength.

In various aspects, the present technology provides an optical sensor device comprising a substrate. A first cavity portion is disposed within the substrate having a first depth, and a second cavity portion is disposed within the substrate and having a second depth. The first cavity portion is juxtaposed to the second cavity portion and the first depth is offset by a predetermined distance from the second depth. A dielectric material is disposed within the first and second cavities.

In another aspect, the present technology provides a self-referencing composite Fabry-Pérot cavity sensor. The sensor includes a substrate defining composite cavity including a first portion juxtaposed to a second portion, wherein the first and second portions are provided having a predetermined depth offset. A polymer is disposed within the cavity. An interference spectrum resulting from a light source of a known wavelength reflecting through the sensor produces a first refractive index from the first portion offset by a second refractive index from the second portion.

In still another aspect, the present technology provides a self-referencing composite Fabry-Pérot cavity sensor comprising a substrate defining a first cavity juxtaposed to a second cavity, wherein the first cavity and second cavity have a predetermined depth offset. A dielectric material is disposed within the first and second cavities. The dielectric material provides a first reflection surface defined by a plane surface level with a bottom of the first cavity, a second reflection surface defined by a plane surface level with a bottom of the second cavity, and a third reflection surface defined by a plane surface flush with both a top of the substrate and a top of the dielectric material. An interference spectrum resulting from light reflecting through the sensor produces a first reflectivity from the first reflection surface, a second reflectivity from the second reflection surface, and a third reflectivity from the third reflection surface.

The present technology also provides a method of detecting a physical parameter using a self-referencing composite Fabry-Pérot cavity sensor. The method comprises providing a substrate including a first polymer filled cavity juxtaposed to a second polymer filled cavity. The first and second polymer filled cavities have respective depths offset by a predetermined distance. The method includes passing a vapor analyte sample over the substrate for detection while introducing a light source into the first and second cavities. A first refractive index is measured from the first cavity and a second refractive index is measured from the second cavity. The method includes analyzing a difference between the first refractive index and the second refractive index and determining the physical parameter.

Still further, the present technology also provides a method of making a self-referencing Fabry-Pérot sensor. The method comprises forming a first cavity in a substrate having a uniform first depth, and forming a second cavity in the substrate juxtaposed to the first cavity and having a uniform second depth. The second depth is offset from the first depth by a predetermined distance. A dielectric material is provided disposed within the first and second cavities.

Further areas of applicability will become apparent from the drawings and description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Figure 3:
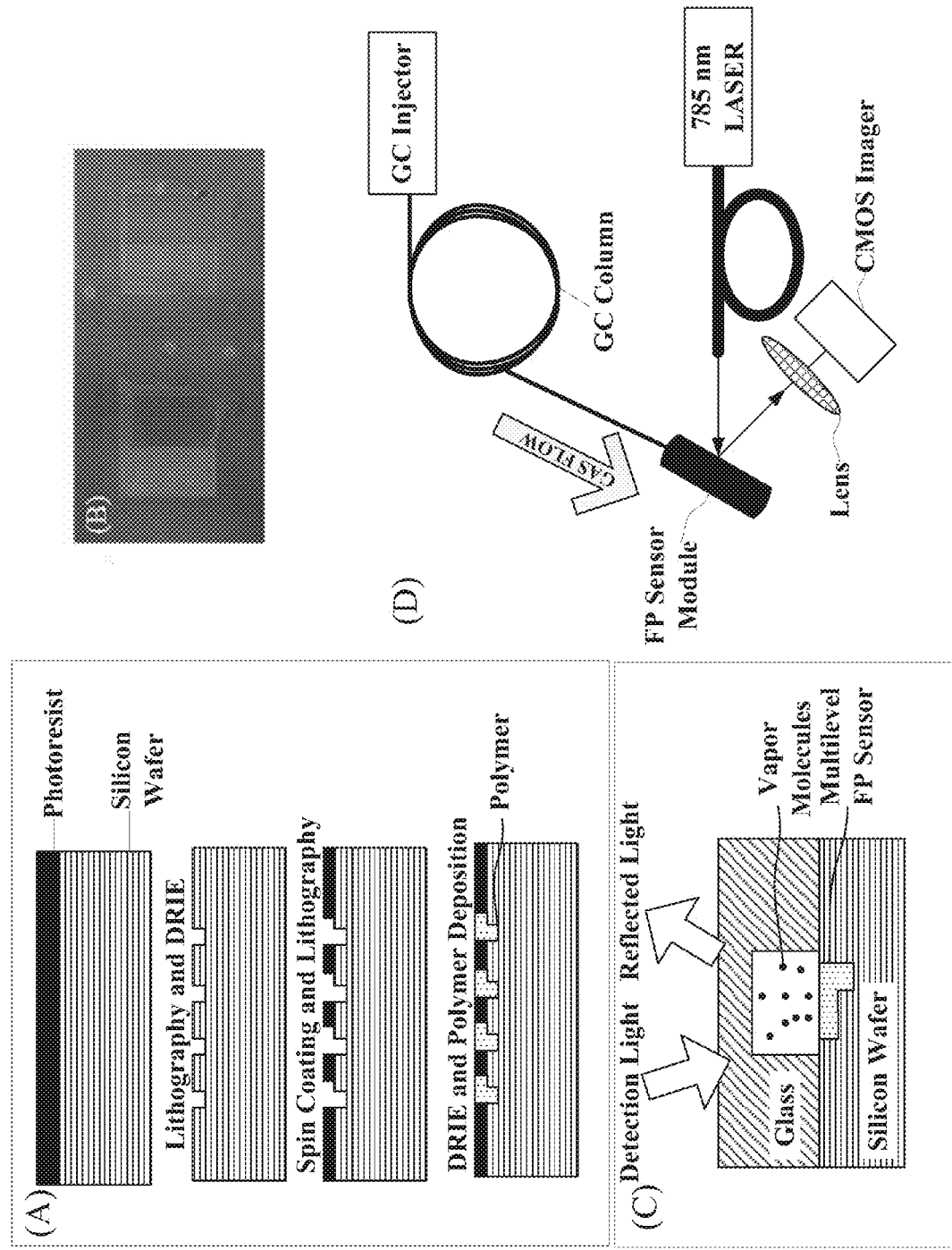
Figure 4:
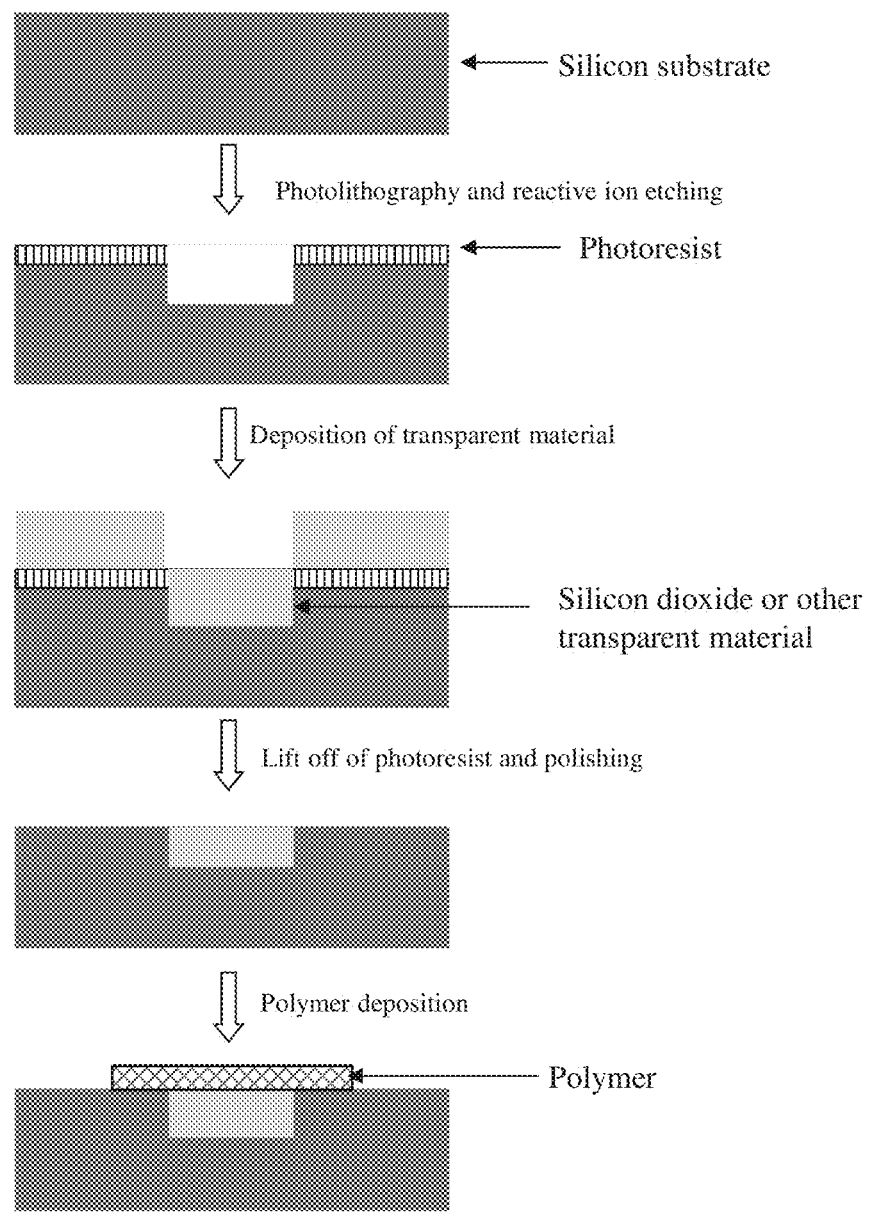
Figure 5:
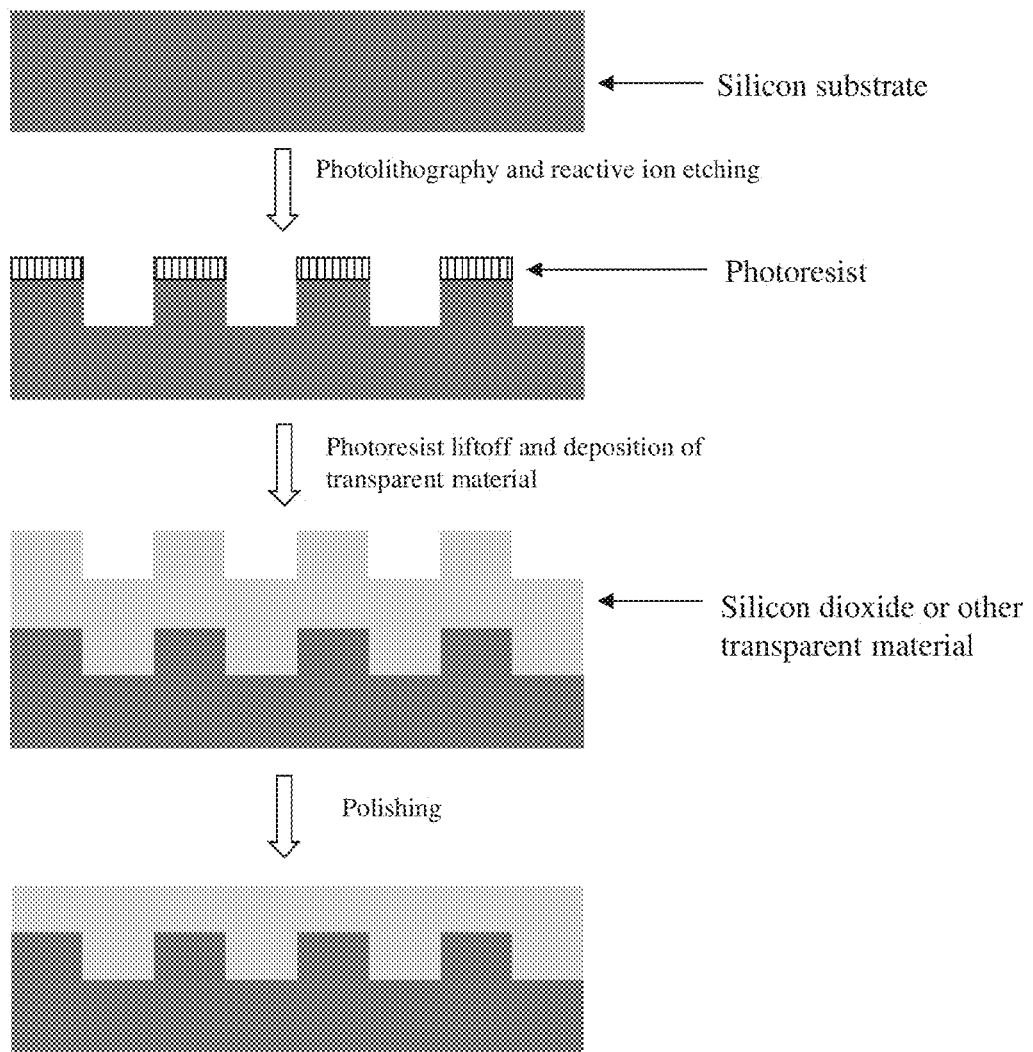

FIGS. 3A-3D illustrate various aspects of fabrication and use of a self-referenced composite Fabry-Pérot cavity sensor according to various aspects of the present disclosure. FIG. 3A illustrates exemplary fabrication steps to create a self-referenced composite Fabry-Pérot cavity sensor according to various aspects of the present disclosure. FIG. 3B illustrates an image of a composite Fabry-Pérot sensor acquired using a CMOS imager. FIG. 3C illustrates a cross-sectional view of a composite Fabry-Pérot sensor on a silicon substrate enclosed by an open bottom glass microfluidic channel. FIG. 3D illustrates a schematic of an experimental setup according to various aspects of the present disclosure;

FIG. 4 illustrates exemplary fabrication steps of a self-referenced composite Fabry-Pérot cavity sensor according to other aspects of the present disclosure;

FIG. 5 illustrates exemplary fabrication steps of a self-referenced composite Fabry-Pérot cavity sensor according to still other aspects of the present disclosure;

FIGS. 6A-6D graphically illustrate the influence of polymer thickness and angle of incidence on the sensor response to the injected vapor analyte according to the present disclosure; and FIGS. 7A-7D graphically illustrate the calculated Δ(nt) at incident angles of both 21° and 26° for three different vapor analytes at various injected masses: acetone, heptane, and toluene according to the present disclosure.

Corresponding reference numerals indicate corresponding parts throughout the several views of the drawings.

DETAILED DESCRIPTION

Example embodiments will now be described more fully with reference to the accompanying drawings.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The terminology used herein is for the purpose of describing particular example embodiments only and is not intended to be limiting. As used herein, the singular forms "a," "an," and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When an element or layer is referred to as being "on," "engaged to," "connected to," or "coupled to" another element or layer, it may be directly on, engaged, connected or coupled to the other element or layer, or intervening elements or layers may be present. In contrast, when an element is referred to as being "directly on," "directly engaged to," "directly connected to," or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

Spatially relative terms, such as "inner," "outer," "beneath," "below," "lower," "above," "upper," and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

Throughout this disclosure, the numerical values represent approximate measures or limits to ranges to encompass minor deviations from the given values and embodiments having about the value mentioned as well as those having exactly the value mentioned. Other than in the working examples provides at the end of the detailed description, all numerical values of parameters (e.g., of quantities or conditions) in this specification, including the appended claims, are to be understood as being modified in all instances by the term "about" whether or not "about" actually appears before the numerical value. "About" indicates that the stated numerical value allows some slight imprecision (with some approach to exactness in the value; approximately or reasonably close to the value; nearly). If the imprecision provided by "about" is not otherwise understood in the art with this ordinary meaning, then "about" as used herein indicates at least variations that may arise from ordinary methods of measuring and using such parameters. In addition, disclosure of ranges includes disclosure of all values and further divided ranges within the entire range, including endpoints given for the ranges.

In various aspects, the present teachings provide a self-referencing composite Fabry-Pérot cavity sensor. The Fabry-Pérot cavity holds great promise in developing on-chip miniaturized sensor arrays for non-destructive, rapid, and sensitive detection. It is particularly attractive for on-column sensing applications in micro-gas chromatography, as it is highly compatible with microfluidics. While the present disclosure may repeatedly refer to aspects involving the detection of vapor analytes and/or using micro-gas chromatography techniques, it should be understood that the present teachings are also applicable with various other optic detection techniques and measurements, including but not limited to strain sensing, temperature sensing, acoustic wave sensing, pressure sensing, protein detection, photo-acoustic imaging, and the like.

Figure 1:
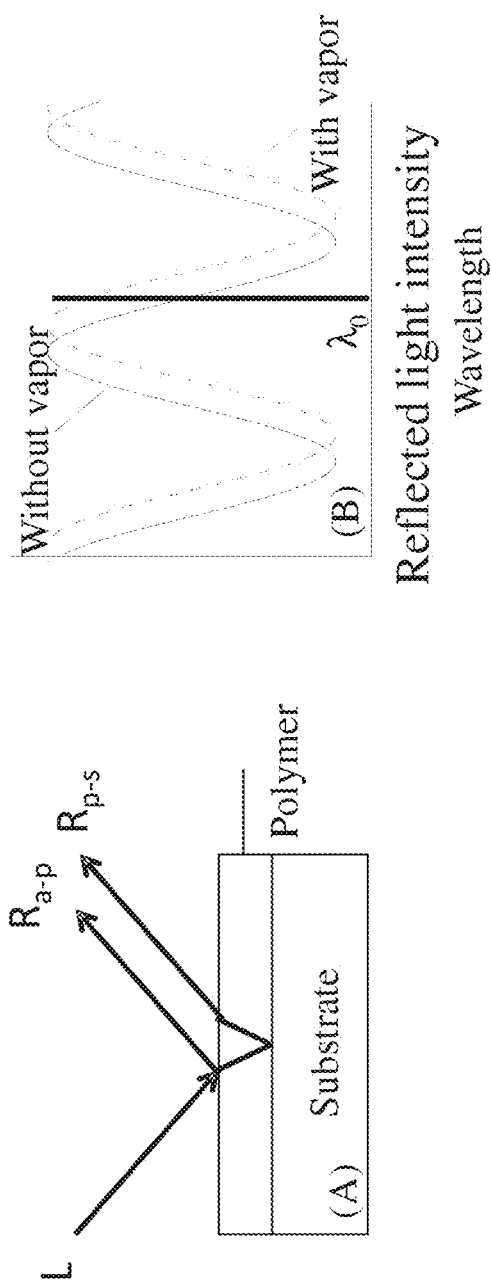
FIG. 1A is a simplified exemplary schematic showing a side view of a conventional Fabry-Pérot cavity sensor.
FIG. 1B is graph illustrating the change in the characteristic Fabry-Pérot spectrum where absorption of analytes by the polymer results in a change in thickness and/or refractive index of the polymer.

In various aspects, a Fabry-Pérot vapor sensor may include a dielectric material, such as a vapor sensitive polymer, coated on a solid substrate. With reference to FIG. 1A, which illustrates a side view of an on-chip Fabry-Pérot sensor, light (L) reflected from an air-polymer interface ($R_{a-p}$) and a polymer-substrate interface ($R_{p-s}$) forms an interference pattern. Once exposed to a vapor analyte sample, the interaction between the polymer and vapor analyte causes a change in the polymer thickness and the refractive index, which in turn results in a change in the reflection spectrum. Thus, by measuring the reflection spectrum shift, the change in the polymer thickness, and the refractive index, the concentration of the analyte can then be quantified. Usually such spectral domain measurements involve a bulky spectrometer, and are often slow and limited by the spectral resolution of the spectrometer. A tunable diode laser has also been employed to measure the Fabry-Pérot sensor spectral shift. While providing a high spectral resolution, the tunable diode laser is expensive and has a limited tuning speed and range.

A different method is to fix an incident laser wavelength at a quadrature point of the Fabry-Pérot interference spectrum and then monitor the light intensity change as shown in FIG. 1B. FIG. 1B illustrates the change in the characteristic Fabry-Pérot spectrum where absorption of analytes by the polymer dielectric material results in a change in thickness and/or refractive index of the polymer. This method is simple, fast, sensitive, and amenable to the integration of all components (light source, sensor, and detector) on a single chip. However, in practice, the light intensity measurement method may encounter various hurdles. For example, while most experimental conditions can be controlled precisely, the thickness of the polymer layer, which is usually deposited on a solid substrate through drop-coating, dip-coating, or spin-coating, may vary significantly from batch to batch. Such variations adversely cause the detection wavelength to deviate from the most sensitive quadrature point and thus result in different detection sensitivities that negate analyte quantitation. This problem is exacerbated when an array of sensors is employed with different polymer coatings that may have different thicknesses (and different refractive indices, as well). For example, simultaneously achieving the optimal detection conditions for all those sensors becomes virtually impossible.

The present technology provides a self-referenced composite Fabry-Pérot cavity sensor that enables precise measurement of the change in the polymer or other dielectric material thickness and refractive index, and hence quantification of analytes, without prior knowledge of the polymer or other dielectric material thickness.

Figure 2:
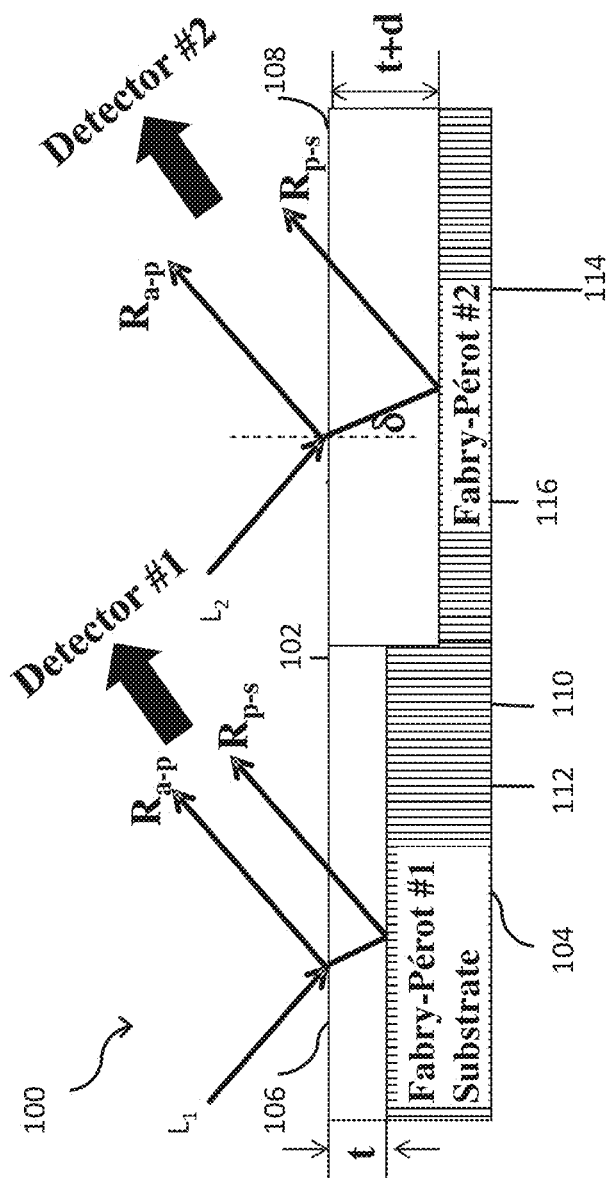
FIG. 2 is an exemplary self-referenced composite Fabry-Pérot cavity sensor according to various aspects of the present disclosure.

An exemplary composite Fabry-Pérot cavity sensor according to various aspects of the present disclosure is illustrated in FIG. 2 and generally referred to by reference number 100. As shown, the sensor comprises a composite cavity 102 defined in a substrate 104 having two independent Fabry-Pérot cavity sensors FP #1 and FP #2 in respective cavity portions 106, 108, that are directly coupled, or juxtaposed to one another, with a slight predetermined thickness in depth offset 110.

The first cavity portion 106 is provided with a first depth and the second portion 108 is provided with a second depth that ultimately provides a polymer or dielectric material thickness offset in the respective cavity portions 106, 108. Although the polymer or dielectric material thicknesses, represented by "t" and "t+d" in FIG. 2 may be unknown, the depth offset 110, also represented by "d" in FIG. 2, can be precisely controlled during fabrication of the sensor, thus allowing one to accurately extract, determine, or otherwise obtain the change in the polymer thickness and refractive index upon exposure to the vapor analyte. In various aspects, the dielectric material is provided having a thickness "t" of less than about 5 μm, for example, from about 0.1 μm to about 3 μm, from about 0.2 μm to about 2.5 μm, from about 0.4 μm to about 2 μm, or from about 0.5 μm to about 1.5 μm. As a guideline in various aspects, the predetermined offset distance "d" may be provided as a multiple of from about 1/10 to about 3 times, or from about 1/10 to about 1 times the wavelength of the light source used for detection. For example, if the light source used has a wavelength of about 600 nm, the offset distance "d" may be from about 60 nm to about 1,800 nm, or from about 60 nm to about 600 nm. It should be understood that the thicknesses and offset distances provided herein are only guidelines, and other variations may be used commensurate with the present teachings.

Once deposited within the composite cavity 102, the dielectric material 103 generally forms three reflection surfaces. A first reflection surface is defined by a plane surface 112 level with a bottom of the first cavity portion 106. A second reflection surface is defined by a plane surface 114 level with a bottom of the second cavity portion 108. A third reflection surface is defined by a plane surface 116 flush with both a top of the substrate 104 and a top of the dielectric material. As light $L_1$ and $L_2$ is reflected through the composite sensor 100, a first reflectivity $R_{p\text{-}s}$ is produced from the first reflection surface 112 to a first detector, a second reflectivity $R_{p\text{-}s}$ is produced from the second reflection surface 114 to a second detector, and respective third reflectivities $R_{a\text{-}p}$ are produced from the third reflection surface 116 to both detectors.

In various aspects, the dielectric material may comprise a vapor sensitive polymer. With a vapor sensitive polymer, the thickness and the refractive index of the polymer vary in response to the vapor analyte, resulting in a change in the reflected intensity of the laser impinged on the sensor. By way of example, a complementary metal-oxide semiconductor (CMOS) sensor may be employed to simultaneously monitor the polymer's response, thus enabling multiplexed detection of a vapor analyte. In other aspects, a charge-coupled device (CCD) or a photo detector array may be used. Non-limiting examples of vapor sensitive polymers include polydimethylsiloxane (PDMS), diphenyldimethylsilicone gum (OV-73); trifluoropropylmethylsilicone gum (OV-215), dimethylphenyl cyano substituted polymer (OV-1701); poly ethylene glycol (PEG), diethylene glycol succinate, and combinations and mixtures thereof.

Because different polymers, such as polar and nonpolar polymers, may have drastically different responses to vapor analytes, it is very common for a gas sensor to incorporate a matrix of polymers in order to enhance the vapor detection specificity. Therefore, it is highly desirable that the Fabry-Pérot cavity is able to accommodate various polymers that may have a wide range of refractive indices.

In various other aspects, for example, when the physical parameter to be analyzed is a function of pressure, the dielectric material may comprise a pressure sensitive polymer. Non-limiting examples of pressure sensitive polymers include polydimethylsiloxane (PDMS), polymethyl-methacrylate (PMMA), piezoelectric polyvinylidene fluoride (PVDF), parylene (including Parylene N, Parylene C), epoxy-based photoresist (SU8), and combinations and mixtures thereof.

Accordingly, the present technology retains all the benefits of standard single Fabry-Pérot sensors, including ease of fabrication and implementation, excellent compatibility with micro-gas chromatography (μGC) components, and rapid detection of analytes, while providing several significant additional advantages.

First, the composite Fabry-Pérot cavity sensor of the present technology is able to precisely measure the thickness and refractive index change of the polymer, regardless of the polymer thickness, refractive index, and light incident angle and wavelength, enabling accurate vapor quantitation. Second, the detection becomes much more flexible, as nearly any wavelength and incident angle can be used without the need for precisely interrogating the sensor at a quadrature. Third, since the composite Fabry-Pérot cavity sensor provides the actual change in polymer thickness and refractive index, it has a larger dynamic range, as compared to the measurement at a quadrature.

With continued reference to FIG. 2, the reflected light intensity at the first Fabry-Pérot cavity sensor (FP #1) is given by:

$$I_1(\lambda) = R_{a\text{-}p} + R_{p\text{-}s} + 2 \times \sqrt{R_{a\text{-}p} R_{p\text{-}s}} \cos \phi \quad \text{(Equation 1)}$$

where the dielectric material is a polymer and $R_{a\text{-}p}$ and $R_{p\text{-}s}$ are the reflectivity at the air-polymer interface and polymer-substrate interface respectively. $\phi = 4\pi \cdot n \cdot t \cdot \cos \delta / \lambda$, where n and t are the polymer refractive index and thickness, respectively, and where $\delta$ and $\lambda$ are the incident angle in the polymer (see FIG. 2) and the wavelength in vacuum, respectively. The light intensity change caused by the vapor-polymer interaction is described by:

$$\Delta I_1 = -8\pi \cos \delta / \lambda \times \sqrt{R_{a\text{-}p} R_{p\text{-}s}} \sin(\phi) \Delta(nt) \quad \text{(Equation 2)}$$

In vapor sensing applications, $\Delta(nt)$ can be used to quantify the analyte. However, in a regular Fabry-Pérot sensor, since the polymer thickness (and hence $\phi$) varies significantly, relating the intensity change, $\Delta I_1$, to $\Delta(nt)$ becomes quite challenging.

This obstacle can be overcome using the present technology by introducing the second Fabry-Pérot cavity sensor (FP #2), directly adjacent to the first cavity sensor (FP #1), where the dielectric material has an additional thickness, d. Similar to Equation 2, and under the assumption that the vapor causes the same polymer response ($\Delta(nt)$) in the second Fabry-Pérot cavity (FP #2), we have, $$\Delta I_2 = -8\pi \cos \delta / \lambda \times \sqrt{R_{a\text{-}p} R_{p\text{-}s}} \sin(\phi + \theta) \Delta(nt) \quad \text{(Equation 3)}$$

where $\theta = 4\pi \cdot n \cdot d \cdot \cos \delta / \lambda$. From Equations (1)-(3), we obtain:

$$\Delta(nt) = A \frac{\sqrt{(\Delta I_1)^2 + (\Delta I_2)^2 - 2\cos\theta \cdot \Delta I_1 \cdot \Delta I_2}}{\sin\theta} \quad \text{(Equation 4)}$$

where A is a constant that contains the information about the light incident angle, wavelength, reflectivities at the two interfaces, and the detector responsivity.

It should be noted that in Equation (4), $\Delta(nt)$ is no longer dependent upon the polymer thickness, t, but only the polymer thickness difference, d, which can be controlled by the offset in depth between the first cavity and the second cavity. As discussed below, the offset in thickness, d, can be created using various micro/nanolithographic methods with high precision and high reproducibility. Therefore, $\Delta(nt)$ can be obtained uniquely by measurement of the reflected light intensity change at the two sensors, thus enabling rapid and accurate detection of physical parameters, such as quantification of the vapor analyte. It should also be noted that in the above derivation, it is assumed that the vapor causes the same polymer response (i.e., $\Delta(nt)$) in both Fabry-Pérot cavity sensors (FP #1 and FP #2). This is true when the vapor is provided in the pulsed format and the exposure time of the polymer to the vapor is short so that only the superficial layer of polymer is affected.

EXAMPLES

One exemplary fabrication procedure for use in making the self-referenced composite Fabry-Pérot cavity sensor of the present technology is illustrated in FIG. 3A, which provides a two-step lithography and deep reactive etching process. Prime grade silicon wafers are spin-coated with a first layer of photoresist and lithographically patterned as shown using a mask aligner, for example, a commercially available MA-6. The wafers are then etched, for example, using a Pegasus deep reactive ion etching ("DRIE") tool, to a uniform etch depth of about 1.3 μm. The two cavities are etched having dimensions of about 400 μm long and about 200 μm wide. The first layer of photoresist is removed, and the wafer is then recoated with photoresist and patterned with precise alignment using the mask aligner. This may be repeated to form an array of cavities disposed within the substrate.

The wafers are once again etched using the DRIE tool to a uniform etch depth of about 1 μm. The resulting etched area is 400 μm long and 400 μm wide, and is aligned to overlap with the previously etched area. This results in a staggered etch, with half of the total etched area etched to a depth of 2.3 μm (i.e., 1.3 μm+1 μm) and the other half etched only 1 μm. FIG. 3B illustrates an image of a composite Fabry-Pérot sensor acquired using a complementary metal-oxide semiconductor (CMOS) imager. The resultant silicon wafer is then diced into pieces having dimensions of about 8 mm×10 mm using an appropriate cutting tool, such as an ADT 7100 dicing saw. These pieces are immersed overnight in sulfuric acid-dichromate solution to oxidize any contaminants, followed by a rinse with deionized water, and finally placed under UV light for about an hour to ensure removal of any residues.

By way of example, OV-215 (Ohio Valley Specialty, 1057) is chosen as a vapor sensing layer because it is a commonly used in many gas chromatography (GC) applications and vapor sensors. A polymer solution is prepared by dissolving the polymer gum in ethyl acetate (where the ratio of OV-215: ethyl acetate equals about 1:3 in mass). The polymer solution is then coated onto the substrate using a spin coater to achieve a smooth layer. For example, the polymer solution is first spun at about 1,300 rpm for about 10 seconds, and then at about 6,000 rpm for about 30 seconds. The spin-coated silicon substrate chip is subsequently heated for about 60 seconds at about 60° C. to remove the solvent. Finally, an open-bottom microfluidic channel (assembled from glass slides and UV-curable optical glue) is used to seal the silicon chip as shown in FIG. 3C. The resulting channel is approximately 1 mm deep and 600 μm wide.

FIG. 3D illustrates an exemplary experimental setup. Analytes are injected using a standard GC injection port and the analyte in a pulsed format is then delivered to the sensor via a 4 m long GC guard column (having an inner diameter of about 250 μm). The detection beam from a Toptica 785 nm laser is aligned using an FC/APC terminated optical fiber and a beam collimator. A Thorlabs CMOS imager, with an acquisition rate of 16 frames per second, is used to acquire the light reflected from each Fabry-Pérot cavity sensor through a lens (Edmund Optics, VZM450). The precise and instantaneous transduction signal from each Fabry-Pérot cavity sensor is captured for post-analysis. All experiments are carried out at room temperature. The mass of the injected analytes is calibrated using a mass spectroscopy system. Helium is used as the carrier gas with a flow rate of 8 mL/min.

FIGS. 4 and 5 provide other detailed exemplary fabrication procedures for use in making the self-referenced composite Fabry-Pérot cavity sensor of the present technology, but with a glass or silicon dioxide type dielectric material disposed within the composite cavity. As shown in FIGS. 4 and 5, a silicon substrate is subjected to photolithography and reactive ion etching, and silicon dioxide or another transparent dielectric material is deposited in the composite cavity. The photoresist is removed and the sensor is polished. As shown in FIG. 4, polymer can be deposited thereon.

In one experimental test, two different incident angles, 21° and 26°, were used to intentionally create a situation that deviates from the traditional quadrature detection scheme (discussed above). The temporal response of each individual sensing element (FP #1 and FP #2 of FIG. 2) of the self-referenced composite Fabry-Pérot cavity sensor is shown in FIGS. 6(A)-(D), which represent the response of individual sensing elements in the composite sensor to 5 ng of acetone at the incident angle of 21° and 26°. Introduction of an analyte from the GC injection port leads to a rapid rise in the measured signal, corresponding to the shift in the interference spectrum. This increase can be attributed to the change in polymer thickness and refractive index as the analyte is absorbed by the polymer. Subsequently, the gas flow in the GC and microfluidic column rapidly purges the analyte from the polymer, resulting in a rapid decline back to the baseline in the measured signal.

The chromatograms reveal a sub-second response time when each individual sensing element (FP #1 and FP #2) is interrogated at both 21° and 26° angles of incidence. However, a comparison among FIGS. 6(A)-(D) shows the strong influence of polymer thickness and angle of incidence on the sensor response to the injected vapor analyte. According to FIGS. 6(A) and (B), at the 21° incident angle, FP #1 has a peak height of 25, while FP #2 has a peak height of 16.5. This difference is due to the different thickness of polymer layer in each individual Fabry-Pérot sensing element, or cavity. A similar difference (28 counts vs. 15 counts) can also be found for FP #1 and FP #2 at the 26° incident angle, as shown in FIGS. 6(C) and (D). Likewise, different incident angles also cause different sensitivities even in the same FP sensor due to the slight light path difference in the polymer. These variations highlight the potential difficulties in obtaining accurate quantitation of the vapor analyte.

In contrast, by using the information gained from the self-referenced composite Fabry-Pérot cavity sensor (i.e., both FP #1 and FP #2), $\Delta(nt)$ can be calculated very precisely. Based on Eq. (4), $\Delta(nt)$ in FIG. 4 is 12.51 and 12.48 for the 21° and 26° incident angle, respectively, which represents a variation of only 0.3%. FIGS. 7(A)-(C) represents the calculated response of the sensors $\Delta(nt)$ at 21° (squares) and 26° (triangles) for three different vapor analytes: (A) acetone, (B) heptane, and (C) toluene, at various injected masses. FIG. 7D is a log-log plot corresponding to FIG. 7C. Error bars are obtained from 5 tests. It clearly shows that for each analyte the calculated $\Delta(nt)$ is nearly equal at both angles of incidence across the entire range of injected mass. Therefore, $\Delta(nt)$ can be used for analyte quantitation regardless of the polymer thickness or incident angle (it should be noted that for some angles at which $\sin(\theta)=0$, this approach becomes invalid).

A linear response is obtained when the injected mass is below approximately 4 ng. At higher injected masses, $\Delta(nt)$ levels off due to the polymer saturation. Additionally, these sensors maintain the high sensitivity and low detection limits previously reported. Given the noise level of 0.38, the detection limit for acetone, heptane, and toluene is about 5.7 pg, 9 pg, and 11 pg or, based on the retention time (~4 s) and the peak width (0.125-0.15 s), as well as the inner diameter and length of the GC column, which correspond to approximately 200 ppb, 335 ppb, and 405 ppb in concentration, respectively. These results are comparable to the best results demonstrated by traditional single Fabry-Pérot sensors under the optimal quadrature detection condition. When used with a vapor detection system, it is expected that the optical sensing technology of the present disclosure has a vapor detection limit of about 100 parts per billion.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. An optical sensor device, comprising:
    a substrate;
    a first cavity portion disposed within the substrate and having a first depth;
    a second cavity portion disposed within the substrate and having a second depth; and
    a dielectric material disposed within the first and second cavity portions,
    wherein the first cavity portion is juxtaposed to the second cavity portion and the first depth is offset by a predetermined distance from the second depth.

2. The optical sensor device of claim 1, wherein the optical sensor is self-referencing.

3. The optical sensor device of claim 1, wherein the optical sensor comprises a vapor detection system having a vapor detection limit of about 100 parts per billion.

4. The optical sensor device of claim 1, wherein the dielectric material comprises a pressure sensitive polymer selected from the group consisting of polydimethylsiloxane, polymethyl-methacrylate, piezoelectric polyvinylidene fluoride, parylene, epoxy-based photoresist, and combinations and mixtures thereof.

5. The optical sensor device of claim 1, wherein the dielectric material comprises a vapor sensitive polymer selected from the group consisting of polydimethylsiloxane, diphenyldimethylsilicone gum, trifluoropropylmethylsilicone gum, dimethylphenyl cyano substituted polymer, poly ethylene glycol, diethylene glycol succinate, and combinations and mixtures thereof.

6. The optical sensor device of claim 1, wherein the dielectric material comprises silicon dioxide.

7. The optical sensor device of claim 1, wherein the dielectric material is provided having a thickness of from about 0.5 μm to about 2.5 μm.

8. The optical sensor device of claim 1 configured for measuring a reflected light intensity of a known wavelength, wherein the predetermined distance in depth offset between the first cavity portion and the second cavity portion is a multiple of from about 1/10 to about 1 times the wavelength.

9. The optical sensor device of claim 1, wherein a concentration of an analyte in a vapor can be quantified without knowledge of a thickness of the dielectric material.

10. The optical sensor device of claim 1, wherein the substrate comprises a silicon wafer.

11. A method of making a self-referencing Fabry-Pérot sensor, the method comprising:
    forming a first cavity in a substrate having a uniform first depth;
    forming a second cavity in the substrate juxtaposed to the first cavity and having a uniform second depth with a predetermined distance offset from the first depth; and
    providing a dielectric material disposed within the first and second cavities.

12. The method of claim 11, further comprising:
    forming a first reflection surface, the first reflection surface defined by a plane surface level with a bottom of the first cavity;
    forming a second reflection surface, the second reflection surface defined by a plane surface level with a bottom of the second cavity; and forming a third reflection surface, the third reflection surface defined by a plane surface flush with both a top of the substrate and a top of the dielectric material.

13. The method of claim 11, wherein providing the dielectric material comprises applying a polymer solution to the substrate using spin coating technology.

14. The method of claim 11, comprising etching the first and second cavities each having dimensions of about 400 µm long and about 200 µm wide, with a depth offset of from about 0.5 µm to about 1.5 µm.

* * * * *